United States Patent
Chiu et al.

(10) Patent No.: US 9,757,372 B2
(45) Date of Patent: Sep. 12, 2017

(54) TOLL-LIKE RECEPTOR 4 ANTAGONISTS AND USE IN AUTOIMMUNE LIVER DISEASES

(71) Applicant: TAIWANJ PHARMACEUTICALS CO., LTD., Zhubei, Hsinchu County (TW)

(72) Inventors: Peter J S Chiu, Mill Creek, WA (US); Mei-chi Hsu, Tainan (TW); Ying-Chu Shih, Chuton Township, Hsinchu county (TW); Edwin S C Wu, Research Triangle Park, NC (US)

(73) Assignee: TaiwanJ Pharmaceuticals Co., Ltd., Zhubel (TW)

( * ) Notice: Subject to any disclaimer, the term of this patent is extended or adjusted under 35 U.S.C. 154(b) by 0 days.

(21) Appl. No.: 15/078,342

(22) Filed: Mar. 23, 2016

(65) Prior Publication Data
US 2016/0287578 A1    Oct. 6, 2016

Related U.S. Application Data

(60) Provisional application No. 62/138,216, filed on Mar. 25, 2015.

(51) Int. Cl.
| | | |
|---|---|---|
| *A61K 31/485* | (2006.01) | |
| *A61K 31/52* | (2006.01) | |
| *A61K 45/06* | (2006.01) | |
| *A61K 31/573* | (2006.01) | |

(52) U.S. Cl.
CPC ............ *A61K 31/485* (2013.01); *A61K 31/52* (2013.01); *A61K 31/573* (2013.01); *A61K 45/06* (2013.01)

(58) Field of Classification Search
USPC ............................................. 514/282
See application file for complete search history.

(56) References Cited

U.S. PATENT DOCUMENTS 4,857,533 A * 8/1989 Sherman ............ A61K 31/485
514/282
7,501,433 B2 * 3/2009 Wu ..................... A61K 31/485
514/281

FOREIGN PATENT DOCUMENTS

| WO | 03/097608 A2 | 11/2003 |
| WO | 2006/029167 A2 | 3/2006 |

OTHER PUBLICATIONS

Cazja, Expert Rev. Gastroenterol. Hepatol. 6(5),603-615 (2012).*
Aoyama T, Paik Y-H, Seki E., "Toll-like receptor signaling and liver fibrosis", Gastroenterol Res Practice, Article ID 192543, 2010:1-8, 2010.
Chuang Y-H, Ridgway WM, Ueno Y, Gershwin, ME., "Animal Models of Primary Biliary Cirrhosis", Clin Liver Dis 12:333-347, 2008.
Czaja AJ., "Current and prospective pharmacotherapy for autoimmune hepatitis", Expert Opin Pharmacother. 15:1715-1736, 2014.

(Continued)

*Primary Examiner* — San-Ming Hui
(74) *Attorney, Agent, or Firm* — Ladas & Parry LLP (57) ABSTRACT

The present invention relates to new medical uses of morphinans such as naltrexone, nalmefene and their related derivatives. The present invention relates to Toll-like receptor 4 (TLR4) antagonist compounds, and pharmaceutical formulations thereof, and use thereof for prevention and treatment of autoimmune liver diseases including but not limited to autoimmune hepatitis.

13 Claims, 2 Drawing Sheets

(56) References Cited

OTHER PUBLICATIONS

Dyson JK, Webb G, Hirschfield GM, Lohse A, Beuers U, Lindor K, Jones DEJ, "Unmet clinical need in autoimmune liver diseases", J Hepatol 62:208-218, 2015.

Ebrahimkhani MR, Kiani S, Oakley F, Kendall T, Shariftabrizi A, Tavangar SM, Moezi L, Payabvash S, Karoon A, Hoseininik H, Mann DA, Moore KP, Mani AR, Dehpour AR, "Naltrexone, an opioid receptor antagonist, attenuates liver fibrosis in bile duct ligated rats", Gut. 55:1606-1616, 2006.

Gong Q, Zhang H, Li JH, Duan LH, Zhong S, Kong XL, Zheng F, Tan Z, Xiong P, Chen G, Fang M, Gong FL, "High-mobility group box 1 exacerbates concanavalin A-induced hepatic injury in mice", J Mol Med (Berl) 88:1289-98, 2010.

Greeneltch KM, Haudenschild CC, Keegan AD, Shi R, "The opioid antagonist naltrexone blocks acute endotoxic shock by inhibiting TNF-$\alpha$ production", Brain Behav Immun 18:476-484, 2004.

He X-S, Ansari AA, Ridgway WM, Coppel RL, Gershwin ME, "New insights to the immunopathology and autoimmune responses in primary biliary cirrhosis," Cell Immunol 239:1-13, 2006.

Hutchinson MR, Zhang Y, Brown K, Coats BD, Shridhar M, Sholar PW, Patel SJ, Crysdale NY, Harrison JA, Maier SF, Rice KC, Watkins LR, "Non-stereoselective reversal of neuropathic pain by naloxone and naltrexone: involvement of toll-like receptor 4 (TLR4)", Eur J Neurosci. 28:20-29, 2008.

Hutchinson MR, Zhang Y, Shridhar M, Evans JH, Buchanan MM, Zhao TX, Slivka PF, Coats BD, Rezvani N, Wieseler J, Hughes TS, Landgraf KE, Chan S, Fong S, Phipps S, Falke JJ, Leinwand LA, Maier SF, Yin H, Rice KC, Watkins LR, "Evidence that opioids may have toll-like receptor 4 and MD-2 effects", Brain Behav Immun. 24:83-95, 2010.

Jaume M, Jacquet S, Cavaillès P, Macé G, Stephan L, Blanpied C, Demur C, Brousset P, Dietrich G, "Opioid receptor blockade reduces Fas-induced hepatitis in mice", Hepatology 40:1136-1143, 2004.

Jeffrey GP, MacQuillan G, Chua F, Galhenage S, Bull J, Young E, Hulse G, O'Neil G, "Hepatitis C virus eradication in intravenous drug users maintained with subcutaneous naltrexone implants", Hepatology. 45:111-117, 2007.

Kawata K, Tsuda M, Yang GX, Zhang W, Tanaka H, Tsuneyama K, Leung P, He XS, Knechtle S, Ansari AA, Coppel RL, Gershwin ME, "Identification of potential cytokine pathways for therapeutic intervention in murine primary biliary cirrhosis", PLoS One. Sep. 10, 2013;8(9):e74225. doi: 10.1371/journal.pone.0074225. eCollection 2013.

Kesar V, Odin JA, "Toll-like receptors and liver disease", Liver Inter 34:184-196, 2014.

Krawitt EL, "Autoimmune hepatitis", N Eng J Med 354:54-66, 2006.

Lin SL, Lee YM, Chang HY, Cheng YW, Yen MH, "Effects of naltrexone on lipopolysaccharide-induced sepsis in rats", J Biomed Sci. 12:431-440, 2005.

Longhi MS, Mitry RR, Samyn M, Scalori A, Hussain MJ, Quaglia A, Mieli-Vergani G, Ma Y, Vergani D, "Vigorous activation of monocytes in juvenile autoimmune liver disease escapes the control of regulatory T-cells", Hepatology. 50:130-42, 2009.

Makol A, Watt KD, Chowdhary VR, "Autoimmune hepatitis: a review of current diagnosis and treatment", Hepat Res Treat 2011;2011:390916. doi: 10.1155/2011/390916. Epub May 15, 2011.

Mao TK, Lian Z-X, Selmi C, Ichiki Y, Ashwood P, Ansari AA, Coppel RL, Shimoda S, Ishibashi H, Gershwin ME, "Altered monocyte responses to defined TLR ligands in patients with primary biliary cirrhosis", Hepatol 42:802-808, 2005.

Matters GL, Harms JF, McGovern C, Fitzpatrick L, Parikh A, Nilo N, Smith JP, "The opioid antagonist naltrexone improves murine inflammatory bowel disease", J Immunotoxicol 5:179-187, 2008.

Mauss S, Berger F, Goelz J, Jacob B, Schmutz G, "A prospective controlled study of interferon-based therapy of chronic hepatitis C in patients on methadone maintenance", Hepatology. 40:120-124, 2004.

Mencin A, Kluwe J, Schwabe RF, "Toll-like receptors as targets in chronic liver disease", Gut 58:704-722, 2009.

Sass G, Heinlein S, Agli A, Bang R, Schümann J, Tiegs G, "Cytokine expression in three mouse models of experimental hepatitis", Cytokine 19, 115-120, 2002.

Shen M, Lu J, Cheng P, Lin C, Dai W, Wang F, Wang C, Zhang Y, Chen K, Xu L, Zhou Y, Guo C, "Ethyl pyruvate pretreatment attenuates concanavalin a-induced autoimmune hepatitis in mice", PLoS One. Feb. 3, 2014;9(2):e87977. doi: 10.1371/journal.pone.0087977.

Smith JP, Stock H, Bingaman S, Mauger D, Rogosnitzky M, Zagon IS, "Low-dose naltrexone therapy improves active Crohn's disease", Am J Gastroenterol. 102:820-8, 2007.

Testro AG, Visvanathan K, "Toll-like receptors and their role in gastrointestinal disease", J Gastroenterol Hepatol. 24:943-54, 2009.

Tiegs G, Hentschel J, Wendel A, "A T cell-dependent experimental liver injury in mice inducible by concanavalin A", J Clin Invest 90:196-203, 1992.

Wang CC, Cheng PY, Peng YJ, Wu ES, Wei HP, Yen MH, "Naltrexone protects against lipopolysaccharide/D-galactosamine-induced hepatitis in mice", J Pharmacol Sci. 108:239-247, 2008.

Wang X, Smith C, "Targeting Toll-like Receptors with Small Molecule Agents", Chem Soc Rev. Jun. 21, 2013; 42(12): 4859-4866. doi:10.1039/c3cs60039d.

Watkins LR, Wang X, Mustafa S, Hutchinson MR, "In vivo veritas: (+)-naltrexones's actions define translational importance", Trends Pharmacol Sci 35:432-433, 2014.

Wu SJ, Yang Y-H, Tsuneyama K, Leung PSC, Illarionov P, Gershwin ME, Chuang Y-H, "Innate immunity and PBC: Activated invariant NKT cells exacerbate murine autoimmune cholangitis and fibrosis", Hepatol 53: 915-925, 2011.

Xu M, Morishima N, Mizoguchi I, Chiba Y, Fujita K, Kuroda M, Iwakura Y, Cua DJ, Yasutomo K, Mizuguchi J, Yoshimoto T, "Regulation of the development of acute hepatitis by IL-23 through IL-22 and IL-17 production", Eur J Immunol. 41:2828-2839, 2011.

Yen MH, Ko HC, Tang FI, Lu RB, Hong JS, "Study of hepatotoxicity of naltrexone in the treatment of alcoholism", Alcohol 38:117-120, 2006.

Zhou RR, Liu HB, Peng JP, Huang Y, Li N, Xiao MF, Wang H, Fan XG, "High mobility group box chromosomal protein 1 in acute-on-chronic liver failure patients and mice with Con A-induced acute liver injury", Exp Mol Pathol. 93:213-219, 2012.

\* cited by examiner

TOLL-LIKE RECEPTOR 4 ANTAGONISTS AND USE IN AUTOIMMUNE LIVER DISEASES

This application claims priority from U.S. application 62/138,216 filed on Mar. 25, 2015, the contents of which are incorporated herein by reference.

BACKGROUND OF THE INVENTION

The present invention relates to new medical uses of morphinans such as naltrexone, nalmefene and their related derivatives. The present invention relates to Toll-like receptor 4 (TLR4) antagonist compounds, and pharmaceutical formulations thereof, and use thereof for prevention and treatment of autoimmune liver diseases including but not limited to autoimmune hepatitis and primary biliary cirrhosis.

In PCT publication WO 03/097608, we have described a number of new medical uses of opioid and opioid-like compounds, including naltrexone. In PCT publication WO WO2006029167, we have described a number of new medical uses of ethylene-6-desoxy-N-cyclopropylmethyl-14-hydroxydihydronormorphine) or nalmefene, a long-acting, orally available, potent narcotic antagonist with pure antagonist activity.

Recent advances in the research of neurodegenerative diseases of the central nervous system have revealed that the opioids may play a role in modulating the expression of inflammatory factors such as proinflammatory cytokines, free radicals and metabolites of arachidonic acid in microglia and in the mediation of immune-related neurodegeneration [*Adv. Exp. Med. Biol.* 402: 29-33 (1996); *Mov. Disord.* 12: 855-858 (1997)] and neuropathic pain [Hutchinson M R, et al. *Eur J Neurosci.* 28:20-299(2008)].

Autoimmune diseases are immune disorders characterized by T cell hyperactivity and B cell overstimulation leading to overproduction of autoantibodies. However, the pathogenesis of various autoimmune diseases remains to be elucidated. Toll-like receptors (TLRs) are pattern recognition receptors which are part of human innate immune system that recognize and mediates early response to tissue injury, followed by activation of the adaptive immune system (Kesar and Odin 2014). Besides these exogenous pathogen-associated molecular patterns (PAMP), TLRs can also bind with damage-associated molecular patterns (DAMP) produced under stress or by tissue damage or cell apoptosis. It is believed that TLRs build a bridge between innate immunity and autoimmunity. There are five adaptors to TLRs including MyD88, TRIF, TIRAP/MAL, TRAM, and SARM. Upon activation, TLRs recruit specific adaptors to initiate the downstream signaling pathways leading to the production of inflammatory cytokines and chemokines. Under certain circumstances, ligation of TLRs drives to aberrant activation and unrestricted inflammatory responses, thereby contributing to the perpetuation of inflammation in autoimmune diseases. In the past, most studies focused on the intracellular TLRs, such as TLR3, TLR7, and TLR9, but recent studies reveal that cell surface TLRs, especially TLR2 and TLR4, also play an essential role in the development of autoimmune diseases and afford multiple therapeutic targets [Clin Rev Allergy Immunol. 47(2):136-47(2014)]. TLR4 is associated with hepatocytes and non-parenchymal cells, including Kupffer cells, myeloid dendritic cells, stellate cells, T-cells, NK cells, and sinusoidal endothelial cells. In recent years, some evidence suggests a likely mediating role of TLR-4 in the pathogenesis and progression of autoimmune liver diseases (AILDs) (He et al 2006; Longhi et al 2009; Mencin et al 2009). Monocytes from patients with PBC produce increased levels of proinflammatory cytokines such as IL-1β, IL-6, etc. when challenged with a variety of ligands, particularly those signaling through TLR4 and TLR5 (Mao et al 2005). Endogenous DAMPs are released subsequent to tissue damage. The ligands for TLR-2 and TLR-4 such as heat-shock proteins, HMGB1, hyaluronan, fibronectin, heparan sulfate and biglycan are produced to mediate sterile inflammation (Moreth et al 2014). The biological characteristics, signaling mechanisms of TLR2/4, the negative regulators of TLR2/4 pathway, and the pivotal function of TLR2/4 in the pathogenesis of autoimmune diseases including rheumatoid arthritis, systemic lupus erythematosus, systemic sclerosis, Sjogren's syndrome, psoriasis, multiple sclerosis, and autoimmune diabetes were recently reviewed by Liu Y, et al. [Clin Rev Allergy Immunol. 47(2):136-47(2014)]. Although TLR 4 is presumed to play the pivotal function of TLR2/4 in the pathogenesis of autoimmune diseases, direct evidence that TLR4 is implicated in AILD is still lacking. In this application, we disclose that TLR antagonists have demonstrated to be of potential in treating AILD.

Autoimmune liver diseases (AILDs), including but not limited to autoimmune hepatitis (AIH) and primary biliary cirrhosis (PBC), are all rare diseases but result in significant long-term morbidity and mortality (Dyson et al 2015). AIH is a chronic inflammatory disease of unknown etiology characterized by the presence of circulating autoantibodies, hypergammaglobulinemia, and necroinflammatory changes on hepatic histology, and a dramatic response to corticosteroid therapy (Makol et al 2011). Type 1 AIH is characterized by the presence of antinuclear antibody (ANA), anti-smooth muscle antibody (SMA), or both; Type 2 AIH is characterized by the presence of anti-liver kidney microsomal 1 (LKM1) and/or anti-LKM3 and/or anti-liver cytosol 1 (LC1) antibodies (Krawitt 2006; Makol et al 2011).

PBC is marked by the slow progressive destruction of the small bile ducts of the liver, with the intralobular ducts affected early in the disease. When these ducts are damaged, bile builds up in the liver (cholestasis) and over time damages the tissue. This can lead to scarring, fibrosis and cirrhosis. Most of the patients seem to have anti-mitochondrial antibodies (AMAs) against pyruvate dehydrogenase complex (PDC-E2), an enzyme complex that is found in the mitochondria (Mencin et al 2009; Testro et al 2009). Overlapping presentation has been observed with AIH and PBC.

Both AIH and PBC are of unknown cause, reflecting a complex interaction between triggering factors (e.g., innate immunity), autoantigens, genetic predispositions and immunoregulatory networks. Steroid/immunosuppressives combination and steroid/ursodeoxycholic acid (UDCA) are respectively frontline therapies for AIH and PBC. A lack of effective and safe drugs is the main drive for innovative novel therapy.

Concanavalin A (Con A), as a T-cell mitogen, causes acute hepatitis by T-cell activation (Tiegs et al 1992; Sass et al 2002; Shen et al 2014). In addition to the infiltration and accumulation of $CD4^+$ T cells, Kupffer cells and natural killer T (NKT) cells, the Con A model is associated with pro-inflammatory cytokines including IL-1β, IL-6, and IFN-γ. Consequently, Con A-induced hepatitis is considered a representative model of autoimmune hepatitis.

Con A-induced hepatitis in mice in which mice are immunized with 2-octynoid acid coupled to BSA/OVA (2-OA-BSA/OVA) is considered excellent models of AIH (Xu et al 2011; Kawata et al 2013). This model is primarily T-cell dependent, driven by IL-23/Th17 pathway, in addition to IFN-γ. Con A hepatitis is sensitive to dexamethasone. High mobility group box chromosomal protein 1 (HMGB), an endogenous TLR4 ligand, is known to aggravate Con A-induced hepatitis, whereas anti-HMGB-1 protected mice from Con A hepatitis (Zhou et al 2012).

SUMMARY OF THE INVENTION

The present invention relates to Toll-like receptor 4 (TLR4) antagonist compounds, and pharmaceutical formulations thereof, and use thereof for prevention and treatment of autoimmune liver diseases including but not limited to autoimmune hepatitis.

The present invention relates to use of a TLR4 antagonist compound according to the formula (I) in treatment of autoimmune liver diseases or conditions or for the production of medicaments, for treatment of such conditions wherein:

(I)

A is OH or $OCH_3$. R is H, $CH_3$, or cyclopropylmethyl, X is oxygen atom, Y is O, CH2, Z is H or OH. The compounds according to the formula (I) can be enantiomers, diastereoisomers, and pharmaceutically acceptable salts thereof.

Formula (I) can be a structure such as one of the following structures:

(Compound A)

or (Compound B)

Particularly preferred is Compound A (naltrexone), the compound (I) wherein A is OH, R is cyclopropylmethyl, X is O, Y is O, and Z is OH; Compound B (nalmefene), the compound (I) wherein A is OH, R is cyclopropylmethyl, X is O, Y is CH2, and Z is OH.

Figure 3:
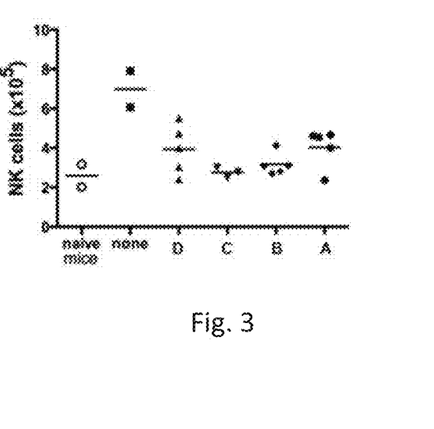
FIG. 3 shows subsets of liver NK cells in a murine model of primary biliary cirrhosis. C57BL/6 mice of 8-10 weeks old were immunized with 2-OA-BSA and α-GalCer at week 0, followed by booster injections at 2, 4, and 8. Oral administration of Compound A (Naltrexone), Compound B (Nalmefene), Compound C (3-methoxymorphinan), and Compound D (3-hydroxymorphinan) at 50 mg/kg bid was on week 4 through week 10. Each value represents individual animals. Some animals were lost due to lunging.
Figure 4:
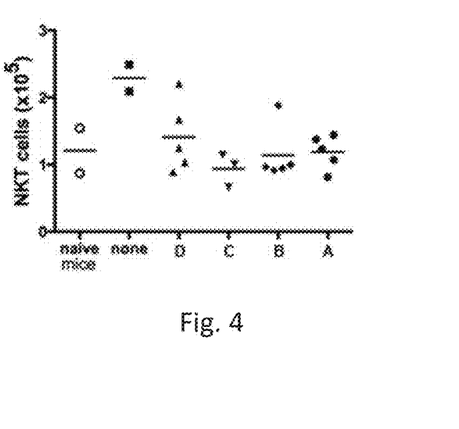
FIG. 4 shows subsets of liver NKT cells in a murine model of primary biliary cirrhosis. C57BL/6 mice of 8-10 weeks old were immunized with 2-OA-BSA and α-GalCer at week 0, followed by booster injections at 2, 4, and 8. Oral administration of Compound A (Naltrexone), Compound B (Nalmefene), Compound C, and Compound D at 50 mg/kg bid was on week 4 through week 10. Each value represents individual animals. Some animals were lost due to lunging.

The elevated NK cells and NKT cells as well as elevated liver mononuclear cells (not shown) in the '2-OS-BSA+α-GalCer' treated mice which were suppressed by Compound A, Compound B, Compound C, and Compound D.

DETAILED DESCRIPTION OF THE INVENTION

Treatments or medicaments produced according to the invention include those for preventing or treating autoimmune liver diseases (AILD) such as, but not limited to autoimmune hepatitis (AIH).

According to other embodiments of the present invention, the present invention relates to methods of preventing or treating AILD such as, but not limited to AIH, comprising administering to a subject in need thereof, a pharmaceutical composition comprising a therapeutically effective amount of one or more of the specified compounds.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, patent applications, patents and other references cited herein are incorporated by reference in their entireties for the teachings relevant to the sentence and/or paragraph in which the reference is presented.

The term "opioid" as used herein refers to compounds that exhibit opium or morphine-like properties, including agonist and antagonist activity wherein such compounds can interact with stereospecific and saturable binding sites in the brain and other tissues. Pharmacological properties have previously included drowsiness, respiratory depression, changes in mood and mental clouding without a resulting loss of consciousness. The term "opioid-like" as used herein refers to compounds that are similar in structure and/or pharmacological profile to known opioid compounds.

"Treat" or "treating" as used herein refers to any type of treatment that imparts a benefit to a patient afflicted with a disease, including improvement in the condition of the patient (e.g., in one or more symptoms), delay in the progression of the condition, prevention or delay of the onset of the disease, etc.

As used herein, a "pharmaceutically acceptable" component (such as a salt, carrier, excipient or diluent) means that the compound or composition is suitable for administration to a subject to achieve the treatments described herein, without unduly deleterious side effects in light of the severity of the disease and necessity of the treatment.

As used herein the term "prophylaxis" means administering a pharmaceutical to a subject prior to the exhibition of relevant symptoms to reduce the risk of a disease manifesting itself or to reduce its severity if it does manifest itself.

"Therapeutically effective amount" as used herein refers to an amount necessary to prevent, delay or reduce the severity of the condition of interest and also includes an amount necessary to enhance normal physiological functioning.

Active compounds of the present invention can be water soluble and can also comprise known water-soluble opioid and opioid-like derivatives.

Compounds of the present invention can possess an asymmetric carbon atom(s) and therefore are capable of existing as enantiomers or diastereoisomers. Thus, compounds of the present invention include enantiomers and diastereoisomers as well as pharmaceutically acceptable salts of the compounds of the present invention.

Active compounds of the present invention can be administered alone or in combination with other therapeutic agents. For example, active compounds of the present invention can be coadministered with compounds now known, or later identified, to be useful for the prevention and or treatment of autoimmune liver diseases (AILD) such as, but not limited to autoimmune hepatitis (AIH). Exemplary compounds include, but are not limited to, antiinflammatories, corticoids (steroids) such as predisone, immunosuppressants such as azathioprine, and the like.

As noted above, naltrexone, nalmefene and dextromethorphan are well documented compounds and commercially available. Other compounds of use in the present invention may be obtained by modification of nalmefene by routine chemical methods or by use of techniques analogous to those described in PCT Publication WO 03/097608.

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. In other particular embodiments, pharmaceutically acceptable salts are formed with malic acid. In particular embodiments, pharmaceutically acceptable salts are formed with hydrochloric acid.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

Pharmaceutical Formulations

The opioid and opioid-like compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

It will be appreciated that certain compounds of the above formulas can possess an asymmetric carbon atom(s) and are thus capable of existing as enantiomers. Unless otherwise specified, this invention includes such enantiomers, including racemates. The separate enantiomers may be synthesized from chiral starting materials, or the racemates can be resolved by procedures that are well known in the art of chemistry such as chiral chromatography, fractional crystallization of diastereometric salts and the like.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter cilia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. In one particular embodiment, a pharmaceutical composition comprises less than 80% by weight of active compound. In other particular embodiments, a pharmaceutical composition comprises less than 50% by weight of active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, tablets, dragees, or syrups each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.01 to 0.2 M active ingredient.

The present invention may also be formulated into a sustained-release preparation. A sustained-release composition includes, but is not limited to, those in which the active ingredient is bound to an ion exchange resin which is optionally coated with a diffusion barrier to modify the release properties of the resin. Carriers and/or diluents which may be used include vaseline, lanoline, glycerin,vegetable oils, or fat emulsions, polyethylene glycols, alcohols, transdermal enhancers, natural or hardened oils or waxes, and combinations of two or more thereof.

Methods of Use

In addition to the compounds of the formulas described herein, the present invention also provides useful therapeutic methods. For example, the present invention provides a method of treating autoimmune liver diseases (AILD) such as, but not limited to autoimmune h Illustrative avians according to the present invention include chickens, ducks, turkeys, geese, quail, pheasant, ratites (e.g., ostrich) and domesticated birds (e.g., parrots and canaries), and include birds in ovo. Chickens and turkeys are preferred.

Any mammalian subject in need of being treated according to the present invention is suitable. Human subjects are preferred. Human subjects of both genders and at any stage of development (i.e., neonate, infant, juvenile, adolescent, adult) can be treated according to the present invention.

As noted above, the present invention provides pharmaceutical formulations comprising the compounds of formulae described herein, or pharmaceutically acceptable salts thereof, in pharmaceutically acceptable carriers for any suitable route of administration, including but not limited to, oral, rectal, topical, buccal, parenteral, intramuscular, intradermal, intravenous, and transdermal administration.

According to the present invention, methods of this invention comprise administering an effective amount of a composition of the present invention as described above to the subject. The effective amount of the composition, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. For example, the compounds of the present invention can be administered to the subject in an amount ranging from a lower limit from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, or 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% by weight of the composition. In some embodiments, the compounds comprise from about 0.05 to about 95% by weight of the composition. In other embodiments, the compounds comprise from about 0.05 to about 60% by weight of the composition. In still other embodiments, the compounds comprise from about 0.05 to about 10% by weight of the composition.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 1 mg/kg to about 50 mg/kg may be employed for oral administration.

In particular embodiments, compounds of the present invention may be administered at a daily dosage of from about 0.1 mg to about 20 mg per kg of animal body weight, which can be given in divided doses q.d. to q.i.d. or in a sustained release form. For humans, the total daily dose may be in the range of from about 1 mg to about 1,400 mg, for example from 1 to 50 mg daily and in other particular embodiments, the total daily dose is in the range of from about 10 mg to about 100 mg. In still other embodiments, the unit dosage forms suitable for oral administration may comprise about 1 mg to about 1,400 mg of the compound optionally admixed with a solid or liquid pharmaceutical carrier or diluent. The compounds of the present invention can be administered in any amount appropriate to administer to the subject for treatment of the condition desired to be treated as determined by one of ordinary skill in the art by reference to the pertinent texts and literature and/or by using routine experimentation. (See, for example, Remington, *The Science And Practice of Pharmacy* (9th Ed. 1995). However, in general, satisfactory results are obtained when the compounds of the invention are administered at a daily dosage of from about 0.1 mg to about 20 mg per kg of animal body weight, preferably given in divided doses 1 to 4 times a day or in sustained release form.

The foregoing is illustrative of the present invention, and is not to be construed as limiting thereof. The invention is defined by the following claims, with equivalents of the claims to be included therein.
Compound A (naltrexone), and Compound B (nalmefene), are all commercially available.

EXAMPLE 1 Inhibition of TLR4 Activation

General Procedure

The secreted alkaline phosphatase reporter is under the control of a promoter inducible by the transcription factor NF-κB. TLR stimulation in the screening is tested by assessing NF-κB activation in the HEK293 cells expressing a given TLR. This reporter gene allows the monitoring of signaling through the TLR, based on the activation of NF-κB. In a 96-well plate (200μL total volume) containing the appropriate cells (25,000-50,000 cells/well), we add 20μL of your sample or the positive control ligands to the wells. For the antagonist assay, the samples are incubated with the cells for 30 minutes prior to adding the appropriate stimulating ligand. The media we add to the wells is designed for the detection of NF-κB induced SEAP expression. After a 16-20 hr incubation we read the OD at 650 nm on a Beckman Coulter AD 340C Absorbance Detector.

TABLE 1

| TLR4 antagonist evaluation* | | |
|---|---|---|
| LPS Conc. | Compound Conc. | % of Inhibition of NF-κB |
| 50 pg/mL | 10 μM (Compound B) | 21% |

TABLE 1-continued

| TLR4 antagonist evaluation* | | |
|---|---|---|
| LPS Conc. | Compound Conc. | % of Inhibition of NF-κB |

*Toll-Like Receptor (TLR4) stimulation is tested by assessing NF-κB activation in HEK293 cells expressing a given TLR4. The activity of the samples are tested on human TLR4 as antagonist. Each ligand is tested at three concentrations on the TLR4 and compared to control ligands (see list below). This step is performed in triplicate (n = 2).

Results

Compound B exhibited weak inhibition of LPS-induced TLR4 activation at various concentrations, TLR4 antagonists. Compound A has been reported to be a TLR4 antagonist by Hutchinson et. al. (Eur J Neurosci. 28:20-29, 2008).

EXAMPLE 2 Animal Models

Experimental Design of Concanavalin A Hepatitis in Mouse

Male BALB/c mice weighing 24±2 g were fasted overnight prior to use. Test compound at 20 and 50 mg/kg and vehicle (10 mL/kg) were administered by gavage (PO) at 24 h, 16 h and 0.5 h before intravenous (IV) injection of Concanavalin A (15 or 20 mg/kg) and at 4 h and 8 h after Con A challenge, whereas dexamethasone at 0.1 mg/kg was administered orally at 0.5 h before and at 4 and 8 h after Con A challenge. The blood was collected at 6 hr. (0.15 mL) and 24 h (0.4 mL) after intravenous administration of Con A. The animals were sacrificed 24 hr after Con A and the liver tissues were harvested for further study.

Serum alanine aminotransferase (ALT) and aspartate aminotransferase (AST) levels were measured spectrophotometrically (optimized UV method). One-way ANOVA followed by Dunnett's test is used to ascertain statistical difference between respective treated groups and vehicle control. The significance criterion is set a $P<0.05$.

Serum Samples (@6 hr)

Six-hr serum samples were kept in storage at −80° C. before shipping back to the Sponsor for further cytokine measurements.

Liver Samples

Terminally the right lateral lobe of liver was harvested. The half of liver was snap frozen with liquid N2 for optional real time RT-PCR; the other half was formalin fixed for possible histopathology and immunochemistry.

Results

Figure 1:
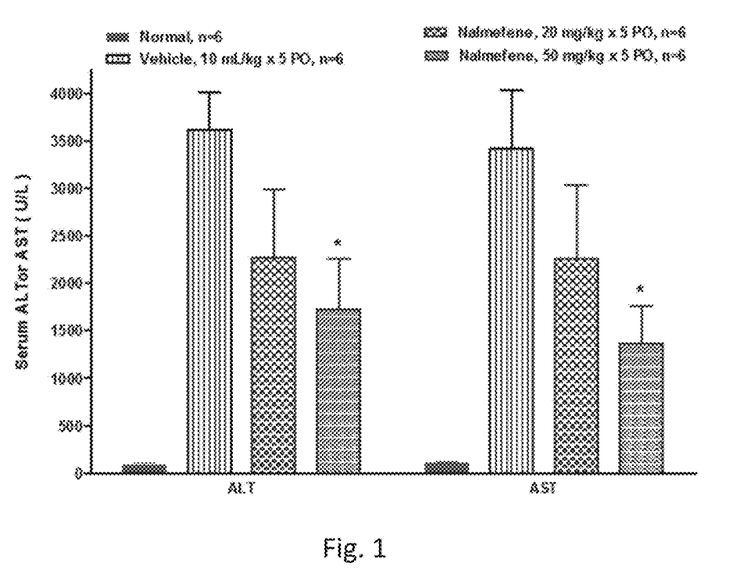
FIG. 1 shows changes in serum alanine transaminase (ALT) and aspartate transaminase (AST) in concanavalin A (Con A)-treated mice. Serum ALT and AST levels were measured 24 h after Con A. All values represent mean±SEM for 6 animals. *P<0.05, vs vehicle control; one way ANOVA followed by Dunnett's test.
Figure 2:
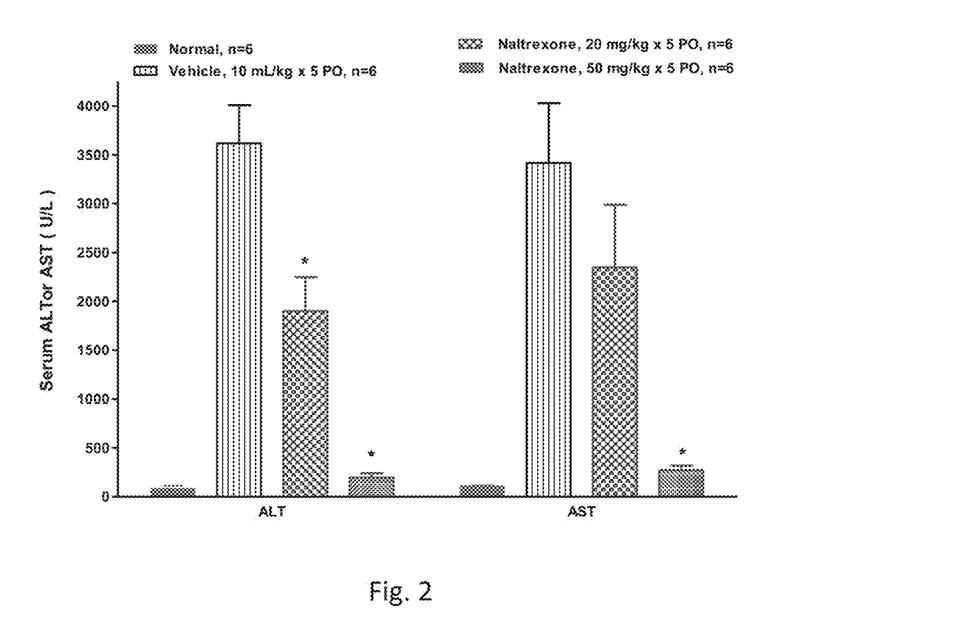
FIG. 2 shows changes in Serum alanine transaminase (ALT) and aspartate transaminase (AST) in concanavalin A (Con A)-treated mice. Serum ALT and AST levels were measured 24 h after Con A. All values represent mean±SEM for 6 animals. *P<0.05, vs vehicle control; one way ANOVA followed by Dunnett's test.

The protectant effect of Compound A (naltrexone) against Con A-induced hepatitis, a murine model of AIH, is shown in FIG. 1. Naltrexone at 20 mg/kg×5 was associated with reduced ALT (−47%) (P<0.05, vs vehicle control; one-way ANOVA and Dunnett's test; n=6) without significant effect on AST (−31%); naltrexone at 50 mg/kg×5 caused significant inhibition of ALT (−95%) and AST (−92%) (P<0.05) (FIG. 1). Similarly, Compound B (nalmefene) at 50 mg/kg (FIG. 2) caused significant (P<0.05) inhibition of Con A-induced elevation of liver enzymes ALT and AST. At the cytokine level, Compound A (naltrexone) at 20 mg/kg was associated with significant (P<0.05 vs vehicle) reduction of inflammatory cytokines IL-5 both in the serum (74%) and liver (21%), as well as IL-6 in the serum (71%) and liver (32%) at 9 hours post Con A challenge. Similarly, Compound B (nalmefene) at 50 mg/kg significantly reduced IL-5 in the serum (64%) and liver (16%) at 6 and 24 hours post Con A challenge, respectively. The significant effect of naltrexone and nalmefene on Con A-induced hepatitis presents strong evidence in support of the use of Compound A (naltrexone) and Compound B (nalmefene) in the treatment of AILDs.

REFERENCES

Aoyama T, Paik Y-H, Seki E. Toll-like receptor signaling and liver fibrosis. Gastroenterol Res Practice. Article ID 192543, 2010:1-8, 2010.

Chuang Y-H, Ridgway W M, Ueno Y, Gershwin, M E. Animal Models of Primary Biliary Cirrhosis. Clin Liver Dis 12:333-347, 2008.

Czaja A J. Current and prospective pharmacotherapy for autoimmune hepatitis. Expert Opin Pharmacother. 15:1715-1736, 2014.

Day S A, Lakner A M, Moore C C, Yen M-H, Clemens M G, Wu E S, Schrum L W. Opioid-like compound exerts anti-fibrotic activity via decreased hepatic stellate cell activation and inflammation. Biochem Pharmacol 81:996-1003, 2011.

Dyson J K, Webb G, Hirschfield G M, Lohse A, Beuers U, Lindor K, Jones D E J. Unmet clinical need in autoimmune liver diseases. J Hepatol 62:208-218, 2015.

Ebrahimkhani M R, Kiani S, Oakley F, Kendall T, Shariftabrizi A, Tavangar S M, Moezi L, Payabvash S, Karoon A, Hoseininik H, Mann D A, Moore K P, Mani A R, Dehpour A R. Naltrexone, an opioid receptor antagonist, attenuates liver fibrosis in bile duct ligated rats. Gut. 55:1606-1616, 2006.

Gong Q, Zhang H, Li J H, Duan L H, Zhong S, Kong X L, Zheng F, Tan Z, Xiong P, Chen G, Fang M, Gong F L. High-mobility group box 1 exacerbates concanavalin A-induced hepatic injury in mice. J Mol Med (Berl) 88:1289-98, 2010.

Greeneltch K M, Haudenschild C C, Keegan A D, Shi R. The opioid antagonist naltrexone blocks acute endotoxic shock by inhibiting TNF-α production. Brain Behav Immun 18:476-484, 2004.

He X-S, Ansari A A, Ridgway W M, Coppel R L, Gershwin M E. New insights to the immunopathology and autoimmune responses in primary biliary cirrhosis. Cell Immunol 239:1-13, 2006.

Hutchinson M R, Zhang Y, Brown K, Coats B D, Shridhar M, Sholar P W, Patel S J, Crysdale N Y, Harrison J A, Maier S F, Rice K C, Watkins L R. Non-stereoselective reversal of neuropathic pain by naloxone and naltrexone: involvement of toll-like receptor 4 (TLR4). Eur J Neurosci. 28:20-29, 2008.

Hutchinson M R, Zhang Y, Shridhar M, Evans J H, Buchanan M M, Zhao T X, Slivka P F, Coats B D, Rezvani N, Wieseler J, Hughes T S, Landgraf K E, Chan S, Fong S, Phipps S, Falke J J, Leinwand L A, Maier S F, Yin H, Rice K C, Watkins L R. Evidence that opioids may have toll-like receptor 4 and MD-2 effects. Brain Behav Immun. 24:83-95, 2010.

Jaume M, Jacquet S, Cavaillès P, Macé G, Stephan L, Blanpied C, Demur C, Brousset P, Dietrich G. Opioid receptor blockade reduces Fas-induced hepatitis in mice. Hepatology 40:1136-1143, 2004.

Jeffrey G P, MacQuillan G, Chua F, Galhenage S, Bull J, Young E, Hulse G, O'Neil G. Hepatitis C virus eradication in intravenous drug users maintained with subcutaneous naltrexone implants. Hepatology. 45:111-117, 2007.

Kawata K, Tsuda M, Yang G X, Zhang W, Tanaka H, Tsuneyama K, Leung P, He X S, Knechtle S, Ansari A A, Coppel R L, Gershwin M E. Identification of potential cytokine pathways for therapeutic intervention in murine primary biliary cirrhosis. PLoS One. 2013 Sep 10;8(9): e74225. doi: 10.1371/journal.pone.0074225. eCollection 2013.

Kesar V, Odin J A. Toll-like receptors and liver disease. Liver Inter 34:184-196, 2014.

Kim H-C, Nabeshima T, Jhoo W K, Ko K H, Kim W K, Shin E J, Cho M, Lee P H. Anticonvulsant effects of new morphinan derivatives. Bioorg Med Chem Lett 11:1651-1654, 2001.

Krawitt E L. Autoimmune hepatitis. N Eng J Med 354:54-66, 2006.

Lang K S, Recher M, Junt T, Navarini A A, Harris N L, Freigang S, Odermatt B, Conrad C, Ittner L M, Bauer S, Luther S A, Uematsu S, Akira S, Hengartner H, Zinkernagel R M. Toll-like receptor engagement converts T-cell autoreactivity into overt autoimmune disease. Nat Med. 11:138-45, 2005.

Lin S L, Lee Y M, Chang H Y, Cheng Y W, Yen M H. Effects of naltrexone on lipopolysaccharide-induced sepsis in rats. J Biomed Sci. 12:431-440, 2005.

Liu Y, Yin H, Zhao M, Lu Q. Clin Rev Allergy Immunol. 2014 Oct;47(2):136-47. TLR2 and TLR4 in autoimmune diseases: a comprehensive review.

Longhi M S, Mitry R R, Samyn M, Scalori A, Hussain Mt Quaglia A, Mieli-Vergani G, Ma Y, Vergani D. Vigorous activation of monocytes in juvenile autoimmune liver disease escapes the control of regulatory T-cells. Hepatology. 50:130-42, 2009.

Makol A, Watt K D, Chowdhary V R. Autoimmune hepatitis: a review of current diagnosis and treatment. Hepat Res Treat 2011;2011:390916. doi: 10.1155/2011/390916. Epub 2011 May 15.

Mao T K, Lian Z-X, Selmi C, Ichiki Y, Ashwood P, Ansari A A, Coppel R L, Shimoda S, Ishibashi H, Gershwin M E. Altered monocyte responses to defined TLR ligands in patients with primary biliary cirrhosis. Hepatol 42:802-808, 2005.

Matters G L, Harms J F, McGovern C, Fitzpatrick L, Parikh A, Nilo N, Smith J P. The opioid antagonist naltrexone improves murine inflammatory bowel disease. J Immunotoxicol 5:179-187, 2008.

Mauss S, Berger F, Goelz J, Jacob B, Schmutz G. A prospective controlled study of interferon-based therapy of chronic hepatitis C in patients on methadone maintenance. Hepatology. 40:120-124, 2004.

Mencin A, Kluwe J, Schwabe R F. Toll-like receptors as targets in chronic liver disease. Gut 58:704-722, 2009.

Moreth K, Frey H, Hubo M, Zeng-Brouwers J, Nastase M-V, Hsieh L T-H, Haceni R, Pfeilschifter J, Iozzo R V, Schaefer L. Biglycan-triggered TLR-2 and TLR-4-signaling exacerbates the pathophysiology of ischemic acute kidney injury. Matrix Biol 35:143-151, 2014.

Sass G, Heinlein S, Agli A, Bang R, Schümann J, Tiegs G. Cytokine expression in three mouse models of experimental hepatitis. Cytokine 19, 115-120, 2002.

Shen M, Lu J, Cheng P, Lin C, Dai W, Wang F, Wang C, Zhang Y, Chen K, Xu L, Zhou Y, Guo C. Ethyl pyruvate pretreatment attenuates concanavalin α-induced autoimmune hepatitis in mice. PLoS One. 2014 Feb 3;9(2): e87977. doi: 10.1371/journal.pone.0087977.

Smith J P, Stock H, Bingaman S, Mauger D, Rogosnitzky M, Zagon I S. Low-dose naltrexone therapy improves active Crohn's disease. Am J Gastroenterol. 102:820-8, 2007.

Testro A G, Visvanathan K. Toll-like receptors and their role in gastrointestinal disease. J Gastroenterol Hepatol. 24:943-54, 2009.

Tiegs G, Hentschel J, Wendel A. A T cell-dependent experimental liver injury in mice inducible by concanavalin A. J Clin Invest 90:196-203, 1992.

Wang C C, Cheng P Y, Peng Y J, Wu E S, Wei H P, Yen M H. Naltrexone protects against lipopolysaccharide/D-galactosamine-induced hepatitis in mice. J Pharmacol Sci. 108:239-247, 2008.

Watkins L R, Wang X, Mustafa S, Hutchinson M R. In vivo veritas: (+)-naltrexones's actions define translational importance. Trends Pharmacol Sci 35:432-433, 2014.

Wu S J, Yang Y-H, Tsuneyama K, Leung P S C, Illarionov P, Gershwin M E, Chuang Y-H.

Innate immunity and PBC: Activated invariant NKT cells exacerbate murine autoimmune cholangitis and fibrosis. Hepatol 53: 915-925, 2011.

Xu M, Morishima N, Mizoguchi I, Chiba Y, Fujita K, Kuroda M, Iwakura Y, Cua D J, Yasutomo K, Mizuguchi J, Yoshimoto T. Regulation of the development of acute hepatitis by IL-23 through IL-22 and IL-17 production. Eur J Immunol. 41:2828-2839, 2011.

Yen M H, Ko H C, Tang F I, Lu R B, Hong J S. Study of hepatotoxicity of naltrexone in the treatment of alcoholism. Alcohol 38:17-120, 2006.

Zhou R R, Liu H B, Peng J P, Huang Y, Li N, Xiao M F, Wang H, Fan X G. High mobility group box chromosomal protein 1 in acute-on-chronic liver failure patients and mice with Con A-induced acute liver injury. Exp Mol Pathol. 93:213-219, 2012.

The invention claimed is:

1. A method of prophylaxis or treating autoimmune hepatitis which comprises administering to a human or animal in need thereof a therapeutic amount of a compound of the formula (I), wherein:

(I)

A is OH or $OCH_3$; R is H, $CH_3$, or cyclopropylmethy; X is the oxygen atom, Y is O, or $CH_2$, Z is H or OH, said compounds being administered as a racemic mixture or as enantiomers, diastereoisomers, or pharmaceutically acceptable salts.

2. The method of claim 1 wherein the compound of Formula (I) has one of the following structures:

(Compound A)

(Compound B)

3. A method as claimed in claim 1, wherein said compound is Compound A (naltrexone).

4. A method as claimed in claim 1, wherein said compound is Compound B (nalmefene).

5. The method of claim 1, wherein the pharmaceutical composition is administered orally.

6. The method of claim 1, wherein the pharmaceutical composition is administered parenterally.

7. The method of claim 1, wherein a compound of formula (I) is administered in combination with other therapeutic agents.

8. The method of claim 7, wherein said other compounds are selected from antiinflammatories, corticoids (steroids), and immunomodulators.

9. The method of claim 8 wherein said other compound is selected from the group consisting of prednisone, and azathioprine.

10. A method as claimed in claim 1 wherein said compound is administered in a daily dose of from 1 mg to 50 mg.

11. The method of claim 8 wherein said other compound is prednisone.

12. The method of claim 9 wherein said compound of formula (I) is naltrexone.

13. The method of claim 11 wherein said compound of formula (I) is naltrexone.

* * * * *